United States Patent

Asselin et al.

Patent Number: 4,510,157
Date of Patent: Apr. 9, 1985

[54] 6,7,8,9-TETRAHYDRO-1H-BENZ(G)INDOL-8-AMINE DERIVATIVES

[75] Inventors: Andre A. Asselin, St. Laurent; Leslie G. Humber, Dollard des Ormeaux, both of Canada

[73] Assignee: Ayerst, McKenna & Harrison, Inc., Montreal, Canada

[21] Appl. No.: 453,306

[22] Filed: Dec. 27, 1982

[51] Int. Cl.³ .................... A61K 31/40; C07D 209/56
[52] U.S. Cl. .................................. 514/411; 548/427; 548/451
[58] Field of Search ................. 548/427, 451; 424/274

[56] References Cited

U.S. PATENT DOCUMENTS

| | | | |
|---|---|---|---|
| 3,845,073 | 10/1971 | Newberry | 548/427 |
| 4,110,339 | 8/1978 | Bach et al. | 424/274 |
| 4,212,804 | 7/1980 | Coppola | 424/274 |
| 4,370,341 | 1/1983 | Asselin et al. | 548/427 |

FOREIGN PATENT DOCUMENTS

| | | |
|---|---|---|
| 2044172 | 3/1971 | Fed. Rep. of Germany . |
| 2740836 | 3/1979 | Fed. Rep. of Germany . |
| 7300871 | 7/1973 | Netherlands . |

OTHER PUBLICATIONS

L. B. Shagalov et al., Chem. Abstr. 91, 56747 v, (1979), for Khim. Geterotsikl. Soedin, (3), 360, (1979).
L. B. Shagalov et al., Chem. Abstr. 89, 146703 r, (1978) for Khim. Geterotsikl. Soedin, (5), 634, (1978).
M. Mottet, Chem. Abstr. 69, 106400 v, (1968), for Ann. Sci. Univ. Besancon, Chim. 1967, (3), No. 4, 29 pp.

*Primary Examiner*—Nicholas S. Rizzo
*Assistant Examiner*—William A. Teoli, Jr.
*Attorney, Agent, or Firm*—Arthur E. Wilfond

[57] ABSTRACT

Herein is disclosed compounds of the formula

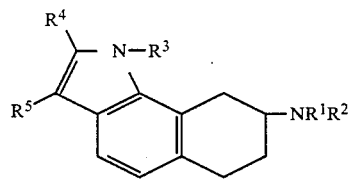

in which $R^1, R^2, R^3, R^4$ and $R^5$ each is hydrogen or lower alkyl, therapeutically acceptable acid addition salts thereof, processes for their preparation, methods of using the compounds and pharmaceutical compositions. The compounds exhibit dopamine-receptor stimulating activity in a mammal and are useful for treating hyperprolactinemia, galactorrhea, amenorrhea, impotence, Parkinsonism, diabetes, acromegaly, hypertension and other central nervous system disorders.

13 Claims, No Drawings

6,7,8,9-TETRAHYDRO-1H-BENZ(G)INDOL-8-AMINE DERIVATIVES

BACKGROUND OF THE INVENTION

This invention relates to novel 6,7,8,9-tetrahydro-1H-benz[g]indol-8-amine derivatives, to therapeutically acceptable acid addition salts thereof, to processes for their preparation, to methods of using the derivatives and to pharmaceutical compositions of the derivatives. These derivatives exhibit dopamine-receptor stimulating activity in a mammal. Thus, they can be useful for treating hyperprolactinemia, galactorrhea, amenorrhea, impotence, Parkinsonism, diabetes, acromegaly, hypertension and other central nervous system disorders which respond to dopamine-receptor stimulation.

A number of 6,7,8,9-tetrahydro-3H-benz[e]indole derivatives are known and described, for example, L. B. Shagalov et al., Chem. Abstr., 91, 56747 v (1979) for Khim. Geterotsikl. Soedin., (3), 360 (1979); L. B. Shagalov et al., Chem. Abstr., 89, 146703 r (1978) for Khim. Geterotsikl. Soedin., (5), 634 (1978); Derwent Publications Ltd., Farmdoc 46000U for Netherland Pat. No. 7,300,871, published July 30, 1973; Derwent Publications Ltd., Farmdoc 24087B for German Offenlegungsshrift No. 2,740,836, published Mar. 22, 1979. The reported compounds lack the substituents on the 6,7,8,9-tetrahydro-1H-benz[g]indole ring system which are characteristic of the compounds of this invention.

RELATED APPLICATIONS

Related hereto is our copending application Ser. No. 215,482, filed Dec. 11, 1980 and now U.S. Pat. No. 4,370,341, which issued Jan. 25, 1983, directed to 6,7,8,9-tetrahydro-3H-benz[e]indol-8-amine derivatives. The instant application relates to 1H-benz[g]indole derivatives as contrasted to the 3H-benz[e]indole derivatives of our copending application.

SUMMARY OF THE INVENTION

The compounds of this invention are represented by formula I

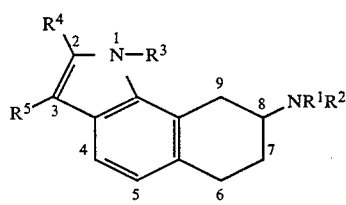

in which $R^1$, $R^2$, $R^3$, $R^4$ and $R^5$ each is hydrogen or lower alkyl having 1 to 5 carbon atoms, or a therapeutically acceptable acid addition salt thereof.

A preferred group of compounds of this invention is repesented by formula I in which $R^1$, $R^2$, $R^3$, $R^4$ and $R^5$ each is hydrogen or lower alkyl having 1 to 3 carbon atoms, or a therapeutically acceptable acid addition salt thereof.

Another preferred group of compounds of this invention is represented by formula I in which $R^1$ and $R^2$ each is hydrogen or lower alkyl having 1 to 5 carbon atoms and $R^3$, $R^4$ and $R^5$ are hydrogen, or a therapeutically acceptable acid addition salt thereof.

A most preferred group of compounds of this invention is represented by formula I in which $R^1$ and $R^2$ each is lower alkyl having 1 to 3 carbon atoms and $R^3$, $R^4$ and $R^5$ are hydrogen, or a therapeutically acceptable acid addition salt thereof.

A pharmaceutical composition is provided by admixing the compound of formula I, or a therapeutically acceptable acid addition salt thereof, with a pharmaceutically acceptable carrier.

The compounds of this invention are used to stimulate dopamine receptors in a mammal in need thereof by administering to the mammal an effective dopamine receptor stimulating amount of a compound of formula I or a therapeutically acceptable acid addition salt thereof. The compounds of this invention are favorably used in combination with an effective amount of an agent commonly used in the treatment of Parkinsonism and related disorders, particularly those selected from bromocriptine, lergotrile, levodopa, combination of levodopa and carbidopa, L-prolyl-L-leucylglycinamide and L-prolyl-N-methyl-D-leucylglycinamide.

The compounds of formula I or a therapeutically acceptable acid addition salt thereof can be prepared by selecting a process from the group of:

(a) when a compound of formula I in which $R^1$ and $R^2$ each is lower alkyl and $R^3$, $R^4$ and $R^5$ are hydrogen is required, reducing a corresponding compound of formula VI

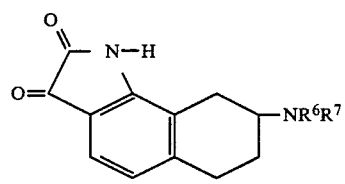

in which $R^6$ and $R^7$ each is lower alkyl with a complex metal hydride;

(b) when a compound of formula I in which $R^1$, $R^4$ and $R^5$ are hydrogen and $R^2$ and $R^3$ each is hydrogen or lower alkyl is required, hydrogenating a compound of formula VII

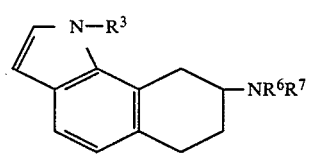

in which $R^3$ is hydrogen or lower alkyl, $R^6$ is benzyl and $R^7$ is benzyl or lower alkyl;

(c) when a compound of formula I in which $R^1$, $R^2$ and $R^4$ each is lower alkyl, $R^3$ is hydrogen and $R^5$ is hydrogen or lower alkyl is required, condensing a compound of formula VIII

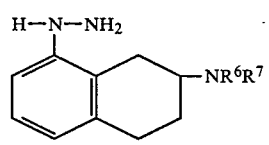

in which $R^6$ and $R^7$ each is lower alkyl with a ketone of the formula

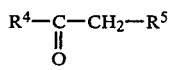

in which $R^4$ is lower alkyl and $R^5$ is hydrogen or lower alkyl according to the Fischer indole method;

(d) when a compound of formula I in which $R^1$ is hydrogen, $R^2$, $R^3$ and $R^5$ each is hydrogen or lower alkyl and $R^4$ is lower alkyl is required, hydrogenating a corresponding compound of formula X

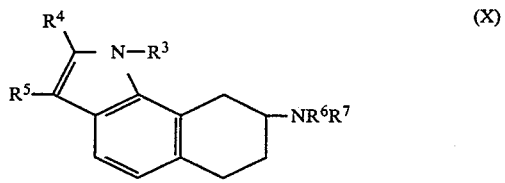

in which $R^3$ and $R^5$ each is hydrogen or lower alkyl, $R^4$ is lower alkyl, $R^6$ is benzyl and $R^7$ is benzyl or lower alkyl;

(e) when a compound of formula I in which $R^1$, $R^2$ and $R^5$ each is lower alkyl and $R^3$ and $R^4$ are hydrogen is required, decarboxylating a corresponding compound of formula XII

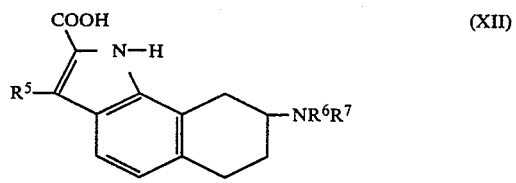

in which $R^5$, $R^6$ and $R^7$ each is lower alkyl;

(f) when a compound of formula I in which $R^1$ and $R^4$ are hydrogen, $R^2$ and $R^3$ each is hydrogen or lower alkyl and $R^5$ is lower alkyl is required, hydrogenating a corresponding compound of formula XIII

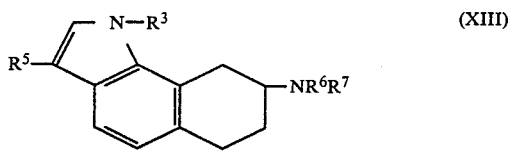

in which $R^3$ is hydrogen or lower alkyl, $R^5$ is lower alkyl, $R^6$ is benzyl and $R^7$ is benzyl or lower alkyl;

(g) when a compound of formula I in which $R^1$, $R^2$ and $R^3$ each is lower alkyl and $R^4$ and $R^5$ each is hydrogen or lower alkyl is required, alkylating the corresponding compound of formula I in which $R^1$ and $R^2$ each is lower alkyl, $R^3$ is hydrogen and $R^4$ and $R^5$ each is hydrogen or lower alkyl;

(h) when a therapeutically acceptable acid addition salt of a compound of formula I is required, reacting the compound of formula I with a therapeutically acceptable acid; and (i) when an individual optical isomer of a compound of formula I in which $R^1$, $R^2$, $R^3$, $R^4$ and $R^5$ each is hydrogen or lower alkyl is required, separating the diastereoisomeric salts and recovering the compound of formula I from the salt.

DETAILED DESCRIPTION OF THE INVENTION

The term "lower alkyl" as used herein means straight and branched chain alkyl radicals containing from one to five carbon atoms and includes methyl, ethyl, propyl, 1-methylethyl, butyl, 1,1-dimethylethyl and pentyl, unless stated otherwise.

The term "complex metal hydride" as used herein means metal hydride reducing agents and includes, for example, lithium aluminum hydride, lithium aluminum hydride-aluminum chloride, aluminum hydride-aluminum chloride, diborane, diisobutylaluminum hydride, borane methyl sulfide and sodium borohydride-aluminum chloride.

Also included in this invention are the stereochemical isomers of the compounds of formula I which result from asymmetric centers contained therein. These isomeric forms may be prepared by chemical methods and are purified readily by crystallization or chromatography.

Individual optical isomers, which might be separated by fractional crystallization of the diastereoisomeric salts formed thereof, for instance, with d- or l-tartaric acid or D-(+)-α-bromocamphor sulfonic acid, are also included.

The compounds of formula I are capable of forming acid addition salts with therapeutically acceptable acids. The acid addition salts are prepared by reacting the base form of the appropriate compound of formula I with one or more equivalents, preferably with an excess, of the appropriate acid in an organic solvent, for example, diethyl ether or an ethanol-diethyl ether mixture. These salts, when administered to a mammal, possess the same pharmacologic activities as the corresponding bases. For many purposes it is preferable to administer the salts rather than the base compounds. Examples of suitable acids to form these salts include: the common mineral acids, e.g., hydrohalic, sulfuric or phosphoric acids; the organic acids, e.g., formic, acetic, maleic, methanesulfonic, malic, citric, or tartaric acid; and acids which are sparingly soluble in body fluids and which impart slow-release properties to their respective salts, e.g., pamoic acid, tannic acid or carboxymethyl cellulose. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The discovery in the mid-1960 3 s of two major dopamine (DA) systems indicated that this neurotransmitter exerted control over a number of physiological functions. Against this background an interest arose to develop DA receptor agonists to study the function of the dopaminergic systems and to evaluate these agonists as possible therapeutic agents in Parkinson's disease and certain neuroendocrine disorders, for example, hyperprolactinemia, galactorrhea, amenorrhea, impotence, hypertension and other central nervous system disorders.

The dopamine-receptor stimulating activity of the compounds of formula I or a therapeutically acceptable acid addition salt thereof is demonstrated in standard pharmacological tests, for example, the antagonism of reserpine-induced catalepsy in mice described by A. M. Johnson et al., Br. J. Pharmac., 56, 59 (1976). In this test method, mice in groups of 10 were injected i.p. with reserpine, 5 mg/kg, 17 hr before the s.c. administration of the test compound. Catalepsy was assessed prior to drug administration and at 30 min, 1 and 2 hr after the test compound, and 1, 2, 3.5 and 5 hr after bromocriptine. Catalepsy was tested as follows: the mice were individually placed on a rubber stopper, 5 cm in diameter and 2½ cm high and observed for 3 min. Mice that remained on the corks during this period were considered to be cataleptic. The results are expressed as (a) dose-response curves, the values representing the percent antagonism of catalepsy during peak activity and (b) as $ED_{50}$'s vs time. Linearity and parallelism of the dose-response relationships were established by analysis of variance. In this test, the following compound of formula I was demonstrated to be an effective dopamine agonist, 6,7,8,9-tetrahydro-N,N-dipropyl-1H-benz[g]indol-8-amine exhibited a peak $ED_{50}$ of $1.9\pm0.6$ milligram per kilogram of body weight upon s.c. administration in the prevention of reserpine-induced catalepsy.

The DA receptor agonists exert a variety of pharmacological effects, some of the most characteristic being the ones that occur in animals in which DA deficiency is brought about to mimic the Parkinsonian syndrome. An important model was developed by U. Ungerstedt, Acta. Physiol. Scand., Suppl. 367, 69–93 (1971) who, by means of unilateral injections of 6-hydroxydopamine (6-OHDA) into the DA pathway, could produce selective lesions of the ascending DA pathways on one side of the brain. Further refinement of this test is described by H. Corridi et al., J. Pharm. Pharmacol., 25, 409–412 (1973); C. J. Pycock and C. D. Marsden, Europ. J. Pharmacol., 47, 167 (1978); and K. Voith and J. R. Cummings, Can. J. Pharmacol., 54, 551 (1976).

Another useful test for dopamine receptor agonists is described by G. P. Smith and R. C. Young in "Advances in Neurology", Vol. 5, F. H. McDowell and A. Barbeau, Eds., Raven Press, New York, pp. 427–432 (1974). In this test, rats exhibit almost complete akinesia in an open field following the bilateral injection of 6-OHDA into the anterolateral hypothalamus. A dopamine receptor agonist can reverse this 6-OHDA-induced hypokinesia.

The above described test methods for dopamine receptor agonists show that the compounds of formula I are active as dopamine receptor agonists. The compounds, thus, can be used clinically in the treatment of hyperprolactinemia, galactorrhoea, amenorrhoea, impotence, diabetes, Parkinsonism, acromegaly, hypertension and other central nervous system disorders, which respond to dopamine-receptor stimulation.

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, or in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as dopamine receptor agonists will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective dopamine receptor stimulating amount of the compounds for i.p. administration usually ranges from about 0.1 mg to about 250 mg per kilogram body weight per day in single or divided doses although as aforementioned variations will occur. However a dosage level that is in the range of from about 0.1 to about 100 mg per kilogram body weight per day in single or divided doses is employed most desirably for i.p. administration in order to achieve effective results. For oral administration, effective amounts can range from about 0.5 to about 250 mg per kilogram body weight per day in single or divided doses preferably about 1.0 to 50 mg per kilogram of body weight per day.

The compound of formula I, or a therapeutically acceptable salt thereof, also can be used to produce beneficial effects in the treatment of Parkinsonism, hyperprolactinemia and related disorders when combined with a therapeutically effective amount of an agent commonly used in the treatment of Parkinsonism, hyperprolactinemia and related disorders. Such agents include, for example, apomorphine and its derivatives, piribedil and its derivatives, dopaminergic ergot derivatives, especially bromocriptine and lergotrile, 2-amino-6,7-dihydroxy-(1,2,3,4)-tetrahydronaphthalene (ADTN), levodihydroxyphenylalanine (levodopa), combination of levodopa with carbidopa, L-prolyl-L-leucylglycinamide (MIF) and its derivatives, especially L-prolyl-N-methyl-D-leucylglycinamide (pareptide), biperiden, cycrimine hydrochloride, procyclidine, trihexyphenidyl hydrochloride, benztropine mesylate, chlorphenoxamine hydrochloride, diphenhydramine hydrochloride, orphenadrine hydrochloride, ethopropazine hydrochloride and the enzymes, monoamine oxidase B and catechol-O-methyl transferase. A combination of the foregoing agents can be substituted for a single agent. Suitable methods of administration, compositions and dosages of the agents are well known in the art; for instance, "Physcan Desk Reference", 32 ed., Medical Economics Co., Oradell, N.J., U.S.A., 1978. When used in combination, the compound of formula I, or its therapeutically acceptable salt, is administered as described previously.

Reaction scheme 1 illustrates a method of preparing the compounds of formula I in which $R^4$ and $R^5$ are hydrogen.

REACTION SCHEME 1

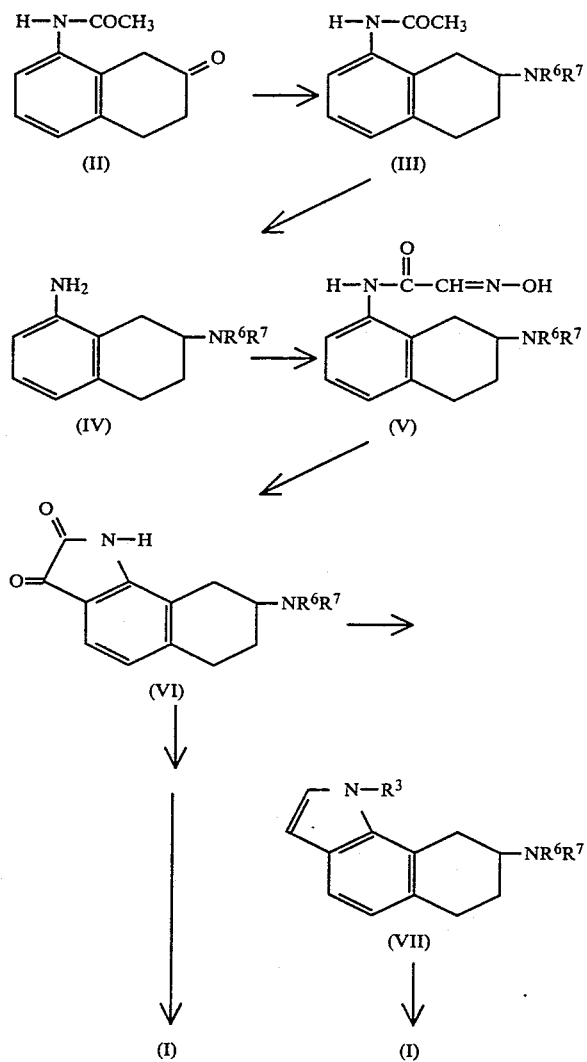

With reference to reaction scheme 1, the compound of formula II is reacted with an excess of a di(lower alkyl)amine and a catalytic amount of p-toluenesulfonic acid in an inert organic solvent, for example, benzene, at about 70° to 90° C. for about one to five days and concurrent removal of water by azeotropic distillation. Reduction of the resulting enamine with hydrogen (about one to three atmospheres of pressure) in the presence of platinum oxide in ethanol gives the corresponding compound of formula III in which $R^6$ and $R^7$ each is lower alkyl. Similarly, reaction of the compound of formula II with a lower alkyl amine, hydrogenation of the resulting enamine and condensation of the so formed secondary amine with benzyl bromide, chloride or iodide gives the corresponding compound of formula III in which $R^6$ is benzyl and $R^7$ is lower alkyl. Another compound of formula III is obtained by reaction of the compound of formula II with hydroxylamine to obtain the oxime, reduction of the oxime with lithium aluminum hydride or nickel aluminum alloy to obtain the primary amine and reaction of the primary amine with benzyl bromide, chloride or iodide to obtain the corresponding compound of formula III in which $R^6$ and $R^7$ are benzyl. Hydrolysis of the compound of formula III with hydrochloric acid at about 80° to 100° C. for about one to five hours gives the corresponding diamine of formula IV in which $R^6$ and $R^7$ are as defined herein.

A solution of the dihydrochloride salt compound of formula IV, about three to four molar equivalents of hydroxylamine hydrochloride and about six to seven molar equivalents of sodium sulfate in water or about one to five percent hydrochloric acid is heated to about 100° C. and a solution of about 1.2 to 10 molar equivalents of chloral hydrate in water is added. The resulting solution is maintained at about 100° C. for about two to ten hours to give the corresponding compound of formula V in which $R^6$ and $R^7$ are as defined herein. Cyclization of the latter compound with concentrated sulfuric acid at about 20° to 80° C. for 0.5 to two hours gives the corresponding compound of formula VI in which $R^6$ and $R^7$ are as defined herein.

Reduction of the compound of formula VI in which $R^6$ and $R^7$ each is lower alkyl with a complex metal hydride gives the corresponding compound of formula I in which $R^1$ and $R^2$ each is lower alkyl and $R^3$, $R^4$ and $R^5$ are hydrogen. This reduction can be achieved conveniently by reacting the compound of formula VI with about ten molar equivalents of lithium aluminum hydride in an inert organic solvent, for example, tetrahydrofuran or dioxane, at 20° to 30° C. for one to ten hours to give the corresponding compound of formula I in which $R^1$ and $R^2$ each is lower alkyl and $R^3$, $R^4$ and $R^5$ are hydrogen. Alkylation of the latter compound of formula I gives the corresponding compound of formula I in which $R^1$, $R^2$ and $R^3$ each is lower alkyl and $R^4$ and $R^5$ are hydrogen. A convenient method of alkylation is the reaction of the compound of formula I with about two molar equivalents of sodium hydride in an inert solvent, preferably tetrahydrofuran, at 20° to 30° C. for 10 to 30 minutes to generate the corresponding anion. Reaction of this anion with a lower alkyl iodide, chloride or bromide at 20° to 60° C. for 5 to 30 hours gives the corresponding compound of formula I in which $R^1$, $R^2$, $R^3$, $R^4$ and $R^5$ are as defined immediately above.

Similarly, reduction of the compound of formula VI in which $R^6$ is benzyl and $R^7$ is benzyl or lower alkyl with the complex metal hydride gives the corresponding compound of formula VII in which $R^3$ is hydrogen, $R^6$ is benzyl and $R^7$ is benzyl or lower alkyl. Alkylation of the latter compound, in the same manner as described above, gives the corresponding compound of formula VII in which $R^3$ is lower alkyl, $R^6$ is benzyl and $R^7$ is benzyl or lower alkyl. Hydrogenation of the compound of formula VII in which $R^3$ is hydrogen or lower alkyl, $R^6$ is benzyl and $R^7$ is benzyl or lower alkyl in the presence of a noble metal hydrogenation catalyst, for example, platinum on carbon, palladium on carbon or platinum oxide, in an inert solvent, for example, methanol or ethanol, gives the corresponding compound of formula I in which $R^1$, $R^4$ and $R^5$ are hydrogen and $R^2$ and $R^3$ each is hydrogen or lower alkyl.

Reaction scheme 2 illustrates a method for converting the compound of formula IV to the compounds of formula I in which $R^4$ and/or $R^5$ are lower alkyl.

REACTION SCHEME 2

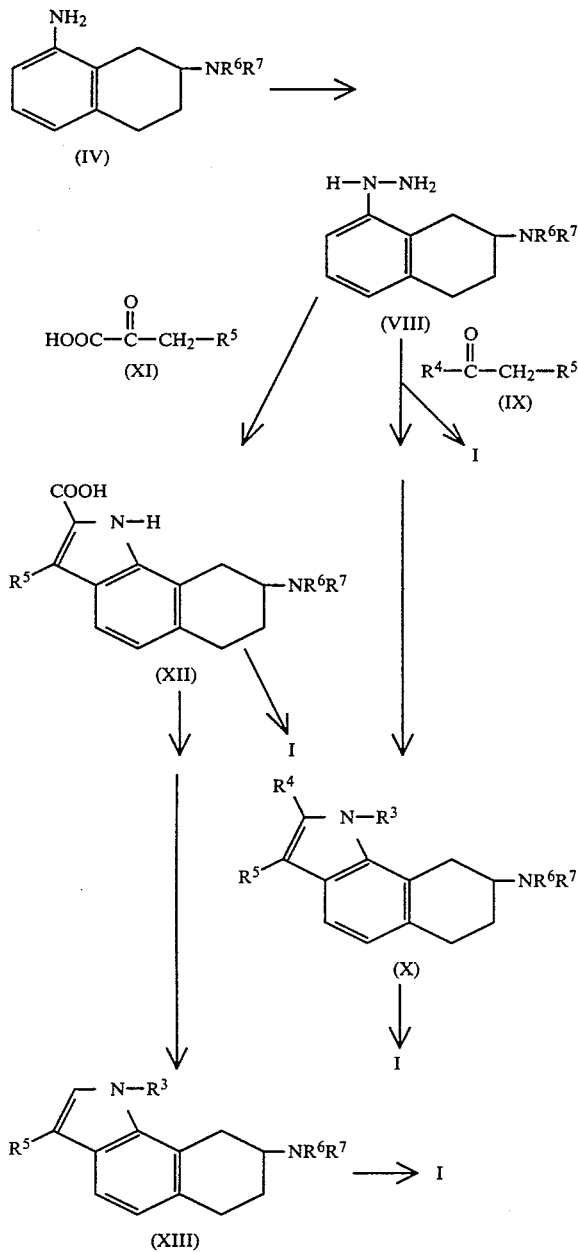

With reference to reaction scheme 2, the diamine of formula IV in which $R^6$ and $R^7$ are as defined herein is converted to the corresponding hydrazine of formula VIII in which $R^6$ and $R^7$ are as defined herein. For this conversion, a solution of the compound of formula IV and about an equimolar amount of sodium nitrite in hydrochloric acid is maintained at about 0° C. for one to five hours. A solution of about two and half molar equivalents of stannous chloride in hydrochloric acid is added at about −5° to −15° C. The mixture is maintained at this temperature for about one to five hours. Thereafter the corresponding compound of formula VIII is isolated.

Condensation of the hydrazine of formula VIII in which $R^6$ and $R^7$ each is lower alkyl with a ketone of formula IX in which $R^4$ is lower alkyl and $R^5$ is hydrogen or lower alkyl according to the Fischer indole synthesis gives the corresponding compound of formula I in which $R^1$, $R^2$ and $R^4$ each is lower alkyl, $R^3$ is hydrogen and $R^5$ is hydrogen or lower alkyl. The indole synthesis is achieved by maintaining a solution of about equal molar quantities of the compounds of formulae VIII and IX in acetic acid at about 100° to 120° C. for about three to ten hours. Similarly, condensation of the compound of formula VIII in which $R^6$ is benzyl and $R^7$ is benzyl or lower alkyl with the ketone of formula IX in which $R^4$ is lower alkyl and $R^5$ is hydrogen or lower alkyl according to the Fischer indole synthesis gives the corresponding compound of formula X in which $R^3$ is hydrogen, $R^4$ is lower alkyl, $R^5$ is hydrogen or lower alkyl, $R^6$ is benzyl and $R^7$ is benzyl or lower alkyl. Alkylation of the latter compound, in the same manner as described above, gives the corresponding compound of formula X in which $R^3$ is lower alkyl and $R^4$, $R^5$, $R^6$ and $R^7$ are as defined immediately above. Hydrogenation of the compound of formula X in which $R^3$ is hydrogen or lower alkyl and $R^4$, $R^5$, $R^6$ and $R^7$ are as defined immediately above, in the same manner as described above, gives the corresponding compound of formula I in which $R^1$ is hydrogen, $R^2$, $R^3$ and $R^5$ each is hydrogen or lower alkyl and $R^4$ is lower alkyl.

A Fischer indole condensation of the compound of formula VIII in which $R^6$ and $R^7$ are as defined herein with a keto-acid of formula XI in which $R^5$ is lower alkyl, in the same manner as described above, gives the corresponding compound of formula XII in which $R^5$ is lower alkyl and $R^6$ and $R^7$ are as defined herein. Decarboxylation of the compound of formula XII in which $R^6$ and $R^7$ each is lower alkyl, preferably with three to ten normal sulfuric acid at 50° to 100° C., yields the corresponding compound of formula I in which $R^1$, $R^2$ and $R^5$ each is lower alkyl and $R^3$ and $R^4$ are hydrogen. Similarly, decarboxylation of the compound of formula XII in which $R^5$ is lower alkyl, $R^6$ is benzyl and $R^7$ is benzyl or lower alkyl gives the corresponding compound of formula XIII in which $R^3$ is hydrogen and $R^5$, $R^6$ and $R^7$ are as defined immediately above. The latter compound can be alkylated, in the same manner as described above, to give the corresponding compound of formula XIII in which $R^3$ is lower alkyl and $R^5$, $R^6$ and $R^7$ are as defined immediately above. Hydrogenation of the compound of formula XIII in which $R^3$ is hydrogen or lower alkyl and $R^5$, $R^6$ and $R^7$ are as defined immediately above, in the same manner as described above, gives the corresponding compound of formula I in which $R^1$ and $R^4$ are hydrogen, $R^2$ and $R^3$ each is hydrogen or lower alkyl and $R^5$ is lower alkyl.

If desired, the compounds of formula I in which $R^1$ and $R^2$ each is lower alkyl, $R^3$ is hydrogen and $R^4$ and $R^5$ each is hydrogen or lower alkyl can be alkylated, in the same manner as described above, to provide the corresponding compound of formula I in which $R^1$, $R^2$ and $R^3$ each is lower alkyl and $R^4$ and $R^5$ each is hydrogen or lower alkyl.

The following examples illustrate further this invention:

EXAMPLE 1

N-[7-(Dipropylamino)-5,6,7,8-tetrahydro-1-naphthalenyl]acetamide (III: $R^6$ and $R^7$=propyl)

Ammonia (750 mL) was collected in a 3 L 3-necked flask supported in a dry ice-acetone bath. Isopropanol (100 mL) was added to it at −78° C., and portionwise 7-methoxy-1-naphthalenamine hydrochloride [50 g, 0.24 mole), described by H. E. Fierz-David et al, Helv. Chim. Acta, 30, 816 (1947)], followed by tetrahydrofuran (100 mL). To the dark solution, sodium metal (25 g) was added piecewise over a period of 20 minutes and the solution turned to light brown yellow color and finally dark blue. After stirring for 15 minutes, methanol (100 mL) was added dropwise and a light brown-yellow suspension was obtained. The ammonia was allowed to evaporate on a steam bath under a stream of nitrogen and then, water (1.2 L) was added. The solid was filtered, washed with water and dried to give a brown compound (34.7 g), used as such for the next step. A sample (3.0 g) was passed through a column of activated magnesium silicate, sold under the trademark FLORISIL, (60 g) using benzene as eluant to give a crystalline compound. It was recrystallized from methanol-water to give 5,8-dihydro-7-methoxy-1-naphthalenamine, mp 84°–85° C.

The latter compound (31.7 g, 0.180 mole) was dissolved in pyridine (180 mL) and cooled in ice. Acetyl chloride (18 mL) was added dropwise, and the suspension was stirred for 30 minutes at 0° C. and poured into ice-water (1 L). The precipitate was filtered and washed with water to give a brownish compound (32.2 g), used as such for the next step. A sample (3.0 g) was triturated with hot benzene (50 mL) and filtered to give a pink solid (2.3 g). It was crystallized from methanol-water and a drop of triethylamine to give N-(5,8-dihydro-7-methoxy-1-naphthalenyl)acetamide (1.95 g), mp 191°–192° C.

The latter compound (29 g, 0.135 mole) was suspended in a mixture of ethanol (300 mL) and 10% hydrochloric acid (50 mL). After stirring for about 5 min, a solution was obtained from which a new precipitate suddenly formed. After stirring for 30 minutes at room temperature, water (1 L) was added. The reaction mixture was made basic with solid sodium carbonate, saturated with sodium chloride and extracted with dichloromethane. The organic extracts were washed with brine, dried and evaporated to give a solid compound (25 g), used as such for the next step. A sample (3 g) was filtered through a column of activated magnesium silicate, sold under the trademark FLORISIL, (90 g) using dichloromethane as eluant. A pale brown compound was obtained and crystallized from dichloromethane and methanol to give N-(7-oxo-5,6,7,8-tetrahydro-1-naphthalenyl)acetamide (2.2 g), mp 203°–205° C.

A solution of the latter compound (17.2 g, 0.085 mol), toluene (400 mL), dipropylamine (45 mL) and p-toluenesulfonic acid (750 mg) in a 1 L round bottom flask equipped with a Dean-Stark apparatus was refluxed overnight. The reaction mixture was then evaporated to dryness to give an enamine intermediate as a solid. It was dissolved in absolute ethanol (250 mL) and treated at 0° C. (compound crystallized out) with portionwise addition of sodium borohydride (4.5 g). The resulting solution was stirred with ice cooling for 4 hours and evaporated to dryness. The residue was diluted with water. The crystalline precipitate was filtered and washed with water to give a beige solid (23 g), used as such for the next step. A sample was filtered through a column of activated magnesium silicate, sold under the trademark FLORISIL, using dichloromethane as eluant and crystallized from hexane to give the title compound: mp 119°–121° C.; NMR (CDCl$_3$)δ 0.85 (t, 6H), 2.15 (s, 3H), 7.0 (m, 3H) and 7.5 (br s, 1H); and Anal. Calcd for $C_{18}H_{28}N_2O$: C, 74.95% H, 9.79% N, 9.71% and Found: C, 74.87% H, 9.64% N, 9.67%

EXAMPLE 2

$N^7,N^7$-Dipropyl-5,6,7,8-tetrahydro-1,7-naphthalenediamine (IV: $R^6$ and $R^7$=propyl)

A suspension of N-[7-(dipropylamino)-5,6,7,8-tetrahydro-1-naphthalenyl]acetamide (described in Example 1, 15.0 g, 0.052 mole) in 10% hydrochloric acid (500 mL) and was heated on a steam bath for 2 hours. The hot solution was filtered through a fluted filter and rinsed with 10% hydrochloric acid. The filtrate was cooled in ice and made basic with concentrated ammonium hydroxide and solid sodium carbonate at the end. The mixture was extracted with dichloromethane and the extracts were dried and evaporated to dryness to give a brown oil (13.8 g). It was taken back in diethyl ether (400 mL) and treated with a solution of hydrogen chloride in diethyl ether (no excess), and the suspension was evaporated to dryness. The residue was suspended in diethyl ether and filtered to afford a light pink solid (14 g), used as such for the next step. A sample (2.9 g) was crystallized twice from methanol-chloroform and diethyl ether to give the hydrochloride salt of the title compound (1.8 g): mp 274°–276° C.; NMR (DMSO-d$_6$)δ 0.93 (t, 6H), 1.78 (m, 6H) and 7.18 (m, 3H); and Anal. Calcd for $C_{16}H_{26}N_2.2HCl$: C, 60.18% H, 8.84% N, 8.77% and Found: C, 60.06% H, 8.65% N, 8.75%.

EXAMPLE 3

2-(Hydroxyimino)-N-[7-(dipropylamino)-5,6,7,8-tetrahydro-1-naphthalenyl]acetamide (V: $R^6$ and $R^7$=propyl)

The $N^7,N^7$-dipropyl-5,6,7,8-tetrahydro-1,7-naphthalenediamine dihydrochloride (described in Example 2, 9.57 g, 0.030 mole) was dissolved in water (90 mL). To the clear solution was added hydroxylamine hydrochloride (6.9 g, 0.10 mole) and sodium sulfate (27.5 g). The reaction mixture was refluxed with stirring for 0.5 hour. To the refluxing solution was added a hot solution of chloral hydrate (6.1 g, 0.041 mol) in water (90 mL) and the combined mixture was refluxed for 3.5 hours. The hot solution was filtered through glass wool and the filtrate was diluted with water (100 mL). The clear solution was cooled in ice-methanol bath and made basic with concentrated ammonium hydroxide. The precipitate was filtered, washed with water and taken up in dichloromethane. The organic solution was dried and evaporated to afford a pale brown foam (7.2 g) of the title compound, used as such for the next step.

EXAMPLE 4

8-(Dipropylamino)-6,7,8,9-tetrahydro-1H-benz[g]indole-1,2-dione (VI: $R^6$ and $R^7$=propyl)

2-(Hydroxyimino)-N-[7-(dipropylamino)-5,6,7,8-tetrahydro-1-naphthalenyl]acetamide (described in Example 3, 7.0 g, 0.022 mol) was added portionwise to a solution of concentrated sulfuric acid (63 mL) and water (6 mL) preheated at 65° C. An exothermic reaction occurred and the temperature went up to 75° C.

The oil bath was removed and the reaction mixture was stirred for 0.5 hour (or until a clear solution was obtained). It was then poured on ice, cooled in ice-methanol bath and made basic with concentrated ammonium hydroxide (200 mL). The precipitate was extracted with chloroform. The organic extracts were dried and evaporated to give a brown orange solid (5.6 g), used as such for the next step. A sample was crystallized twice from methanol and water to afford an orange solid of the title compound: mp 189°–191° C.; NMR (CDCl$_3$)δ 0.88 (t, 6H), 1.45 (m, 6H), 1.7–3.3 (m, 9H), 6.76 (d, 1H), 7.27 (d, 1H) and Anal. Calcd for C$_{18}$H$_{24}$N$_2$O$_2$: C, 71.96% H, 8.05% N, 9.32% and Found: C, 71.42% H, 7.96% N, 9.56%.

EXAMPLE 5

6,7,8,9-Tetrahydro-N,N-dipropyl-1H-benz[g]indol-8-amine (I: R$^1$ and R$^2$=propyl and R$^3$, R$^4$ and R$^5$=H)

In a 3-necked flask, under nitrogen and ice cooling, was added successively dry diethyl ether (325 mL), lithium aluminum hydride (2.6 g) and 8-(dipropylamino)-6,7,8,9-tetrahydro-1H-benz[g]indole-1,2-dione (described in Example 4, 3.9 g, 0.013 mol) portionwise over a period of 5 minutes. The reaction mixture was stirred at room temperature for 1 hour and cooled in ice. The excess lithium aluminium hydride was destroyed by dropwise addition of ethyl acetate (90 mL). Rochelle salts solution (50 mL) was added dropwise until a gummy precipitate separated and the supernatant solution was decanted. The precipitate was washed several times with ethyl acetate and the washings were combined with the supernatant solution. After drying over magnesium sulfate, the solution was evaporated to afford a dark oil (3.45 g). It was passed through a column of silica gel (1:20) using diethyl ether to give a pink oil (2.1 g). It was taken up in diethyl ether and treated with a solution of hydrogen chloride in diethyl ether. The suspension was evaporated to dryness and the residue was dissolved in hot methanol. Diethyl ether was added and the crystalline precipitate was recrystallized from methanol and diethyl ether to give the hydrochloride salt of the title compound: mp 264°–268° C.; NMR (DMSO-d$_6$)δ 0.95 (t, 6H), 1.77 (m, 6H), 3.08 (m, 8H), 3.53 (m, 1H), 6.35 (s, 1H), 6.70 (d, 1H), 7.2 (s, 1H) and 7.3 (d, 1H); and Anal. Calcd for C$_{18}$H$_{26}$N$_2$.HCl: C, 70.45% H, 8.87% N, 9.13% and Found: C, 70.70% H, 8.82% N, 9.19%.

We claim:

1. A compound of the formula

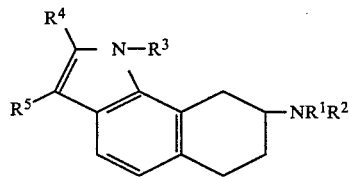

(I)

in which R$^1$, R$^2$, R$^3$, R$^4$ and R$^5$ each is hydrogen or lower alkyl having 1 to 5 carbon atoms, or a therapeutically acceptable acid addition salt thereof.

2. A compound of claim 1 wherein R$^1$, R$^2$, R$^3$, R$^4$ and R$^5$ each is hydrogen or lower alkyl having 1 to 3 carbon atoms, or a therapeutically acceptable acid addition salt thereof.

3. A compound of claim 1 wherein R$^1$ and R$^2$ each is hydrogen or lower alkyl having 1 to 5 carbon atoms and R$^3$, R$^4$ and R$^5$ are hydrogen, or a therapeutically acceptable acid addition salt thereof.

4. A compound of claim 1 wherein R$^1$ and R$^2$ each is lower alkyl having 1 to 3 carbon atoms and R$^3$, R$^4$ and R$^5$ are hydrogen, or a therapeutically acceptable acid addition salt thereof.

5. 6,7,8,9-Tetrahydro-N,N-dipropyl-1H-benz[g]indol-8-amine, a compound of claim 1 wherein R$^1$ and R$^2$ are propyl and R$^3$, R$^4$ and R$^5$ are hydrogen.

6. A pharmaceutical composition for stimulating dopamine-receptors, which comprises a therapeutically acceptable amount of a compound of claim 1, or a therapeutically acceptable acid addition salt thereof, and a pharmaceutically acceptable carrier therefor.

7. A method of stimulating dopamine-receptors in a mammal in need thereof, which comprises administering to said mammal an effective dopamine receptor stimulating amount of a compound of claim 1 or a therapeutically acceptable acid addition salt thereof.

8. The pharmaceutical composition of claim 6 wherein said compound is 6,7,8,9-tetrahydro-N,N-dipropyl-1H-benz[g]indol-8-amine, or a therapeutically acceptable acid addition salt thereof.

9. The method of claim 7 wherein said compound is 6,7,8,9-tetrahydro-N,N-dipropyl-1H-benz[g]indol-8-amine, or a therapeutically acceptable acid addition salt thereof.

10. The method of claim 7 for treating Parkinsonism.

11. A compound of the formula

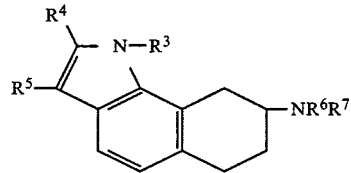

in which R$^3$, R$^4$ and R$^5$ each is hydrogen or lower alkyl, R$^6$ is benzyl and R$^7$ is benzyl or lower alkyl.

12. A compound of the formula

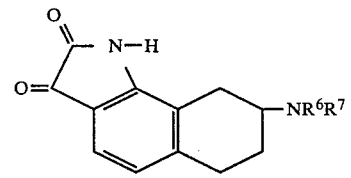

in which R$^6$ and R$^7$ each is benzyl or lower alkyl.

13. A compound of claim 12 wherein R$^6$ and R$^7$ each is lower alkyl.

* * * * *